United States Patent
Kodama et al.

(10) Patent No.: US 10,509,025 B2
(45) Date of Patent: Dec. 17, 2019

(54) POOR PHYSICAL CONDITION DETERMINATION DEVICE, METHOD, AND RECORDING MEDIUM STORED WITH PROGRAM

(71) Applicant: TANITA CORPORATION, Tokyo (JP)

(72) Inventors: Miyuki Kodama, Tokyo (JP); Ayumi Sano, Tokyo (JP); Naotaka Minagawa, Tokyo (JP); Yasuhiro Kasahara, Tokyo (JP)

(73) Assignee: Tanita Corporation, Tokyo (JP)

( * ) Notice: Subject to any disclaimer, the term of this patent is extended or adjusted under 35 U.S.C. 154(b) by 112 days.

(21) Appl. No.: 14/602,963

(22) Filed: Jan. 22, 2015

(65) Prior Publication Data
US 2015/0212062 A1   Jul. 30, 2015

(30) Foreign Application Priority Data
Jan. 27, 2014 (JP) ................. 2014-012526

(51) Int. Cl.
| | |
|---|---|
| *G01N 7/00* | (2006.01) |
| *G01N 21/00* | (2006.01) |
| *G01N 27/00* | (2006.01) |
| *G01N 31/00* | (2006.01) |
| *G01N 1/22* | (2006.01) |
| *G01N 33/497* | (2006.01) |

(52) U.S. Cl.
CPC ... *G01N 33/497* (2013.01); *G01N 2033/4975* (2013.01); *Y10T 436/200833* (2015.01); *Y10T 436/202499* (2015.01)

(58) Field of Classification Search
CPC ............ G01N 1/22; G01N 7/00; G01N 21/00; G01N 27/00; G01N 31/00; G01N 33/00
USPC ............. 422/50, 83, 84, 85, 86, 87, 88, 89; 436/43, 128
See application file for complete search history.

(56) References Cited

U.S. PATENT DOCUMENTS

| | | | | |
|---|---|---|---|---|
| 5,260,219 A | * | 11/1993 | Fritz | ............... A61B 5/00 435/12 |
| 2003/0208133 A1 | * | 11/2003 | Mault | ............... 600/532 |

(Continued)

FOREIGN PATENT DOCUMENTS

| | | |
|---|---|---|
| JP | 2008-295921 A | 12/2008 |
| JP | 2009-175963 A | 8/2009 |

(Continued)

OTHER PUBLICATIONS

Office Action issued in corresponding Chinese Patent Application No. 201510041105.6 dated Oct. 28, 2016.

(Continued)

*Primary Examiner* — Brian J. Sines
(74) *Attorney, Agent, or Firm* — Morgan, Lewis & Bockius LLP

(57) ABSTRACT

The invention provides a poor physical condition determination device, method, and program enabling simple determination of a physical condition level.

A poor physical condition determination device 10 acquires a ketone concentration measurement measuring ketone excreted from a user, determines a physical condition level related to the physical condition of the user based on the acquired ketone concentration measurement, and outputs a determination result.

12 Claims, 10 Drawing Sheets

(56) References Cited

U.S. PATENT DOCUMENTS

| | | | |
|---|---|---|---|
| 2007/0093786 A1* | 4/2007 | Goldsmith et al. | 604/890.1 |
| 2009/0260986 A1* | 10/2009 | Wang et al. | 204/403.04 |
| 2014/0221802 A1* | 8/2014 | Choi | A61B 5/14532 600/365 |
| 2015/0025811 A1* | 1/2015 | Kodama et al. | 702/19 |

FOREIGN PATENT DOCUMENTS

| | | |
|---|---|---|
| JP | 2010-268864 A | 12/2010 |
| WO | 2013/038959 A1 | 3/2013 |

OTHER PUBLICATIONS

Office Action issued in corresponding Japanese Patent Application No. 2014-012526 dated Oct. 24, 2017.

* cited by examiner

| DETERMINATION | SAFE | CAUTION REQUIRED | WARNING | DANGER |
|---|---|---|---|---|
| CONCENTRATION RANGE (ppb) | LESS THAN $a$ | $a$ OR GREATER BUT LESS THAN $b$ | $b$ OR GREATER BUT LESS THAN $c$ | $c$ OR GREATER |

FIG.5

| ΔTHIS TIME - PREVIOUS TIME [ppm] | ELAPSED TIME FROM TIME OF PREVIOUS MEASUREMENT (DAYS) | | | | |
|---|---|---|---|---|---|
| | 1 DAY OR LESS | 2 TO 4 DAYS | 5 TO 7 DAYS | 8 TO 13 DAYS | 14 TO 31 DAYS |
| LESS THAN 1000 | a1 | b1 | c1 | d1 | e1 |
| 1000 TO 2000 | a2 | b2 | c2 | d2 | e2 |
| 2000 TO 3000 | a3 | b3 | c3 | d3 | e3 |
| 3000 OR GREATER | a4 | b4 | c4 | d4 | e4 |

POOR PHYSICAL CONDITION DETERMINATION DEVICE, METHOD, AND RECORDING MEDIUM STORED WITH PROGRAM

CROSS-REFERENCE TO RELATED APPLICATION

This application is based on and claims the benefit of priority of the prior Japanese Patent Application No. 2014-012526, filed on Jan. 27, 2014, the entire contents of which are incorporated herein by reference.

BACKGROUND

Technical Field

The present invention relates to a poor physical condition determination device, method, and program.

Related Art

When dieting, it is not uncommon for continued abstinence from food or excessive dietary restrictions to have an adverse impact on health. Technology has been proposed to ascertain an individual's nutritional state, and to provide dieting advice.

For example, Patent Document 1 proposes technology to assist sensible dieting by providing nutritional information based on dietary contents input by a user.

Patent Document 2 proposes technology capable of measuring the amount of in-breath acetone and hydrogen gas to determine points for lifestyle improvement linked to combating obesity and normalizing the intestinal environment when dieting.

PATENT DOCUMENTS

Patent Document 1: Japanese Patent Application Laid-Open (JP-A) No. 2009-175963
Patent Document 2: JP-A No. 2008-295921

However, in the technology described in Patent Document 1, inputting dietary contents is labor-intensive, and results cannot be obtained simply. Although the technology described in Patent Document 1 includes functions for inputting body weight and body fat percentage, there is no function to call for caution relating to poor physical condition accompanying a sudden drop in body weight.

In the technology described in Patent Document 2, there is no function to prevent excessive dieting such as skipping meals, and so determination of the presence of a dangerous state cannot be made when measuring in-breath acetone or the like. The technology described in Patent Document 2 can therefore not be used in the prevention of, for example, infant malnutrition, or ketonuria during sudden fevers.

SUMMARY

An object of the present invention is to provide a poor physical condition determination device, method, and program enabling simple determination of a physical condition level.

In order to address the above issues, a poor physical condition determination device of the present invention includes a ketone concentration acquisition section that acquires a ketone concentration measurement measuring ketone excreted from a user, a determination section that determines a physical condition level related to the physical condition of the user based on the ketone concentration measurement acquired by the ketone concentration acquisition section, and an output section that outputs a determination result by the determination section.

Configuration may be made such that the determination section determines a poor physical condition level related to poor physical condition of the user as the physical condition level based on a comparison result between the ketone concentration measurement and at least one predetermined threshold value, or based on plural ketone concentration measurements measured in the past and including the ketone concentration measurement.

Configuration may be made such that the threshold value is provided for each user attribute including at least one of gender, age, build, or body composition, and the determination section determines the poor physical condition level according to the user attribute.

Configuration may be made such that the determination section determines a diet level related to dieting by the user as the physical condition level based on a comparison result between the ketone concentration measurement and at least one predetermined threshold value, or based on plural ketone concentration measurements measured in the past and including the ketone concentration measurement.

Configuration may be made such that the determination section determines the diet level based on a comparison result between the ketone concentration measurement and at least one predetermined threshold value, or based on a difference or ratio between the ketone concentration measurement measured a previous time and the ketone concentration measurement measured this time.

Configuration may be made such that the determination section determines the diet level based on a difference or ratio between the ketone concentration measurement measured a previous time and the ketone concentration measurement measured this time, and elapsed time from the previous measurement to the current measurement.

Configuration may be made such that the determination section determines the diet level based on a comparison result between the ketone concentration measurement measured before a meal and the ketone concentration measurement measured after a meal.

Configuration may be made such that the determination section determines whether or not a rebound has occurred as the diet level based on a comparison result between a variation curve expressing variation in the plural ketone concentration measurements, and a predetermined rebound curve expressing variation in the ketone concentration measurements when a rebound from a diet has occurred.

Configuration may be made such that the determination section determines the diet level based on a comparison result between an equation expressing the plural ketone concentration measurements measured for the user, and an equation expressing ketone concentration measurements of ketone concentration measured for subjects performing normal dieting.

Configuration may be made further including a measurement section that measures ketone excreted from the user.

The ketone excreted from the user may be acetone contained in breath exhaled from the user.

A poor physical condition determination method of the present invention includes acquiring a ketone concentration measurement measuring ketone excreted from a user, determining a physical condition level related to a physical condition of the user based on the acquired ketone concentration measurement, and outputting a determination result.

A poor physical condition determination program of the present invention is a poor physical condition determination program that causes a computer to execute processing, the processing including acquiring a ketone concentration measurement measuring ketone excreted from a user, determining a physical condition level related to a physical condition of the user based on the acquired ketone concentration measurement, and outputting a determination result.

Advantageous Effects of Invention

The present invention exhibits the advantageous effect of enabling simple determination of a physical condition level.

BRIEF DESCRIPTION OF DRAWINGS

FIG. 4 is a diagram illustrating an example of a poor physical condition level determination standard.

FIG. 5 is a diagram illustrating an example of a diet level determination standard.

DESCRIPTION OF EMBODIMENTS

Explanation follows regarding an exemplary embodiment of the present invention.

Figure 1:
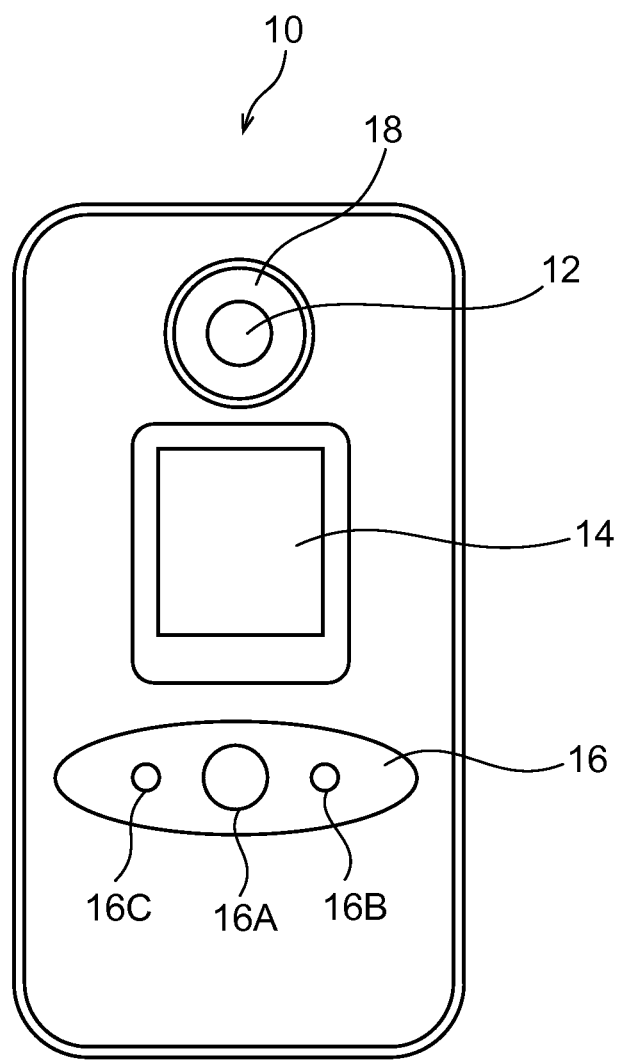
FIG. 1 is a diagram of the external appearance of a poor physical condition determination device.

FIG. 1 is a diagram of the external appearance of a poor physical condition determination device 10 according to the present exemplary embodiment. As illustrated in FIG. 1, the poor physical condition determination device 10 includes a measurement section 12, a display section 14, and an operation section 16. The poor physical condition determination device 10 according to the present exemplary embodiment is, as an example, a portable device that is convenient to be carried around.

The measurement section 12 measures the concentration of ketone excreted from a user (referred to below as ketone concentration). Ketone is a collective name employed for acetoacetic acid, 3-hydroxy acetic acid (β-hydroxy acetic acid), and acetone, and represents at least one thereof.

In the present exemplary embodiment, explanation is given of a case in which the measurement section 12 is, as an example, configured with an acetone detection sensor that detects acetone in the breath of a user. The user is able to measure the acetone concentration of exhaled breath by blowing air into a blow-in hole 18. In order to facilitate collection of exhaled air, the blow-in hole 18 may be a mouthpiece type shaped to be capable of being held in the mouth, or may be a mask type shaped to be capable of collecting exhaled air in an unconscious state.

The display section 14 is configured, for example, by a liquid crystal panel or the like. Various screen images are displayed on the display section 14, such as various setting screen images, the measurement results of acetone concentration measured by the measurement section 12, and advice information based on the measured acetone concentration. The display section 14 may also be configured including a touch panel function, and may be configured to enable operation by directly touching the screen.

The operation section 16 is configured including plural operation buttons, and FIG. 1 illustrates an example of a case in which there are 3 individual operation buttons 16A to 16C provided.

The operation button 16A functions, as an example, as a button to operate to switch the power source of the poor physical condition determination device 10 ON/OFF, and to make selections on various screen images.

The operation button 16B functions, as an example, as a button to input data on various screen images.

The operation button 16C functions, as an example, as a button to instruct reading of past measurement results and the like.

Figure 2:
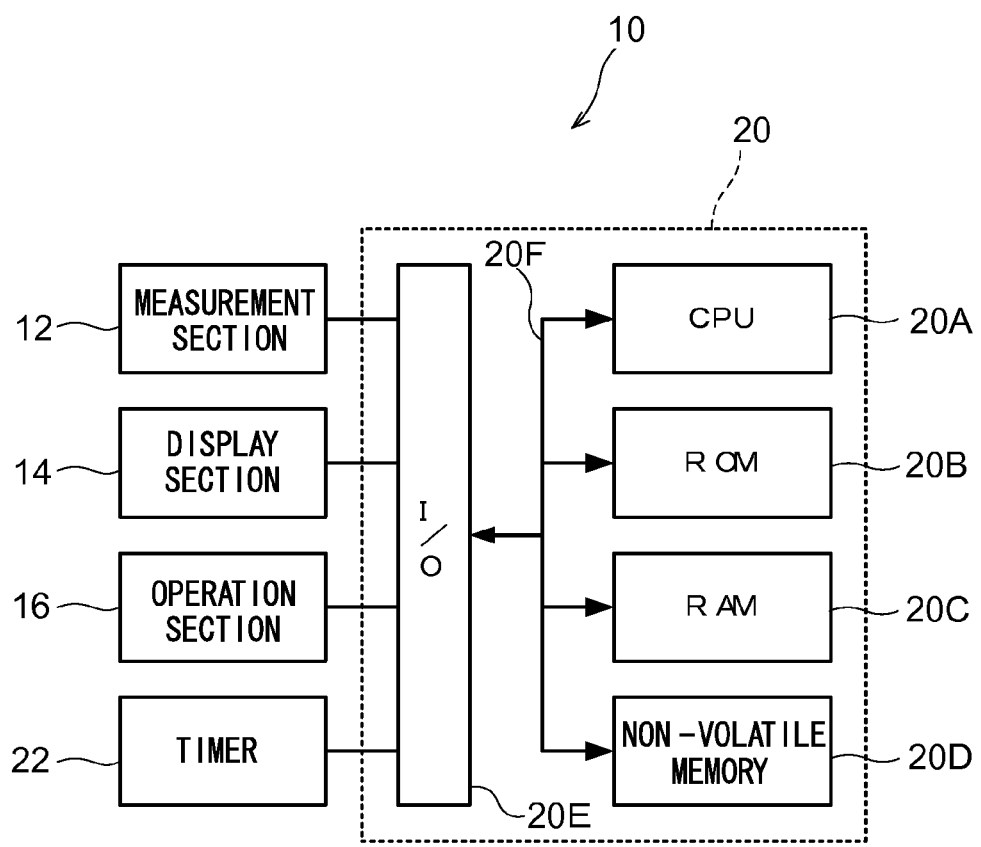
FIG. 2 is a block diagram of a poor physical condition determination device.

FIG. 2 is a block diagram of the poor physical condition determination device 10. As illustrated in FIG. 2, the poor physical condition determination device 10 includes a controller 20. The controller 20 is configured including a Central Processing Unit (CPU) 20A, Read Only Memory (ROM) 20B, Random Access Memory (RAM) 20C, non-volatile memory 20D, and an input-output (I/O) interface 20E, each connected together through a bus 20F. In this case, a poor physical condition determination program that causes the CPU 20A of the controller 20 to execute poor physical condition determination processing, explained later, is, for example, pre-written to the non-volatile memory 20D, and read into and executed by the CPU 20A. The poor physical condition determination program may be provided on a recording medium, such as a CD-ROM, memory card, or the like, or may be downloaded from a server, not illustrated in the drawings.

The measurement section 12, the display section 14, the operation section 16, and a timer 22 are connected to the I/O interface 20E. The timer 22 includes a function to acquire the current time, and a timing function to time a set duration.

Figure 3:
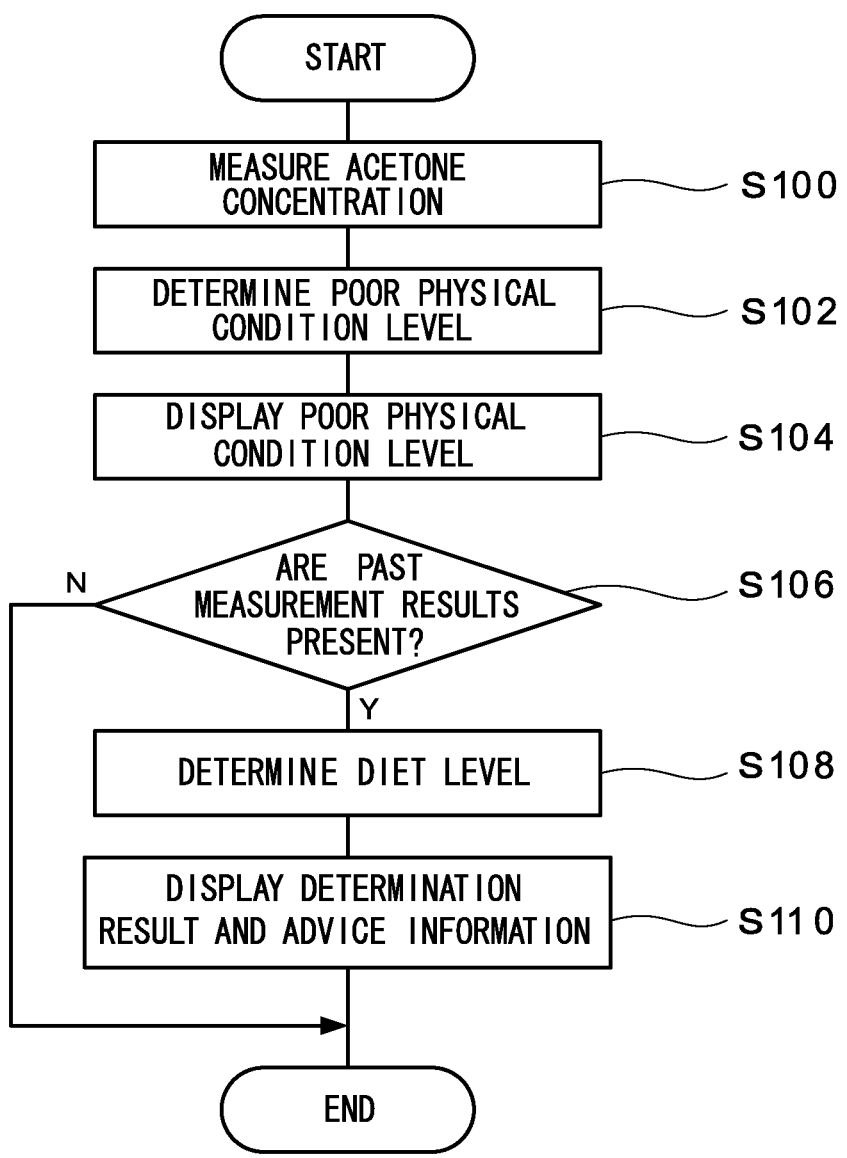
FIG. 3 is a flowchart of processing by a poor physical condition determination program.

Explanation next follows, as operation of the present exemplary embodiment, regarding processing by the poor physical condition determination program executed by the CPU 20A of the controller 20, with reference to the flowchart illustrated in FIG. 3. The processing in FIG. 3 is executed when a user operates the operation section 16 of the poor physical condition determination device 10, and instructs execution of the poor physical condition determination program.

First, at step S100, acetone concentration is measured. More specifically, first a message to start measuring acetone concentration is displayed on the display section 14 after a predetermined time (for example 10 seconds) has elapsed, and the timer 22 is instructed to time a predetermined duration.

Then when notified by the timer 22 that the predetermined duration has elapsed, a blow-in start message instructing air to be exhaled through the blow-in hole 18 is displayed on the display section 14, and the measurement section 12 is instructed to start measuring the acetone concentration. The user exhales air into the blow-in hole 18 when the blow-in start message is displayed on the display section 14.

The measurement section 12 measures the acetone concentration of the air exhaled into the blow-in hole 18 and outputs the measurement to the controller 20. The measured acetone concentration is stored in the non-volatile memory 20D together with the current time acquired from the timer 22.

At step S102, a level of poor physical condition is determined based on the acetone concentration measured at step S100. The acetone concentration of acetone that is a byproduct of fat metabolism may be thought of as corresponding to the fat burn amount. The acetone concentration is lower when there is surplus sugar energy present in the body, and the acetone concentration is higher when there is not enough sugar energy present in the body. Sometimes a low blood-sugar state arises and there is a high acetone concentration when there is a poor physical condition such as malnutrition or running a fever. For example, in infants there is a concern that a low blood-sugar state might arise and ketonuria occur due to malnutrition or a sudden fever.

In the present exemplary embodiment the current poor physical condition level is determined based on a poor physical condition level determination standard 30, such as illustrated in FIG. 4. The poor physical condition level determination standard 30 illustrated in FIG. 4 is, for example, stored in advance in the non-volatile memory 20D. In the example illustrated in FIG. 4, the concentration range of acetone concentration is divided into 4 levels, and the measured acetone concentration is determined to be "safe" when less than a, to be "caution required" when a or greater but less than b, to be "warning" when b or greater but less than c, and to be "danger" when c or greater.

Although in the example of FIG. 4 the concentration range of acetone concentration is divided into 4 levels, the manner in which the concentration range is divided is not limited thereto, and it may be divided into 2 levels, 3 levels, or 5 or more levels. A poor physical condition level determination standard may also be provided for each individual personal attribute including at least one of gender, age, build, or body composition.

At step S104, the poor physical condition level determined at step S102 is displayed on the display section 14. The poor physical condition level may be notified using at least one of light, vibration, or an alert sound.

A user can thereby be easily notified of the poor physical condition level simply by measuring the acetone concentration in exhaled air. This thereby enables, for example, early discovery of poor physical conditions such as malnutrition or fever in infants in the home. It is moreover also possible to determine the onset of ketonuria in infants at the scene of a medical emergency without taking a blood or urine sample, enabling an increase in efficiency to be achieved in a medical emergency, and enabling the burden on a patient to be reduced.

At step S106, determination is made as to whether or not a measurement result of past acetone concentration is stored in the non-volatile memory 20D. Processing transitions to step S108 if stored, and the present routine is ended if not stored.

At step S108, determination of diet level is made based on past acetone concentrations and the current acetone concentration is measured at step S100. Explanation follows regarding the diet level determination method.

In a first diet level determination method, determination of the diet level is made based on a diet level determination standard 40, such as the example illustrated in FIG. 5.

In the example illustrated in FIG. 5, the diet level is set according to a difference Δ between the acetone concentration measured this time and the acetone concentration measured the previous time from the acetone concentrations measured in the past, and the elapsed time from the time of the previous measurement to the time of the current measurement. For example, when the difference Δ is less than 1000, the diet level is determined to be "a1" when the elapsed time from the time of the previous measurement to the time of the current measurement is a day or less, and the diet level is determined to be "e1" when the elapsed time from the time of the previous measurement to the time of the current measurement is from 14 to 31 days. Thus the diet level differs according to the elapsed time from the time of the previous measurement to the time of the current measurement even when there is the same difference Δ value.

The diet level is, for example, expressed numerically, with progression of the diet expressed by the numerical values getting higher. This thereby enables determination of excessive dieting when the diet level is too high. The respective diet levels in the diet level determination standard illustrated in FIG. 5 are determined, for example, from test results for many test subjects.

Determination of the diet level described above is by extracting from the diet level determination standard 40 the diet level corresponding to the difference Δ, between the acetone concentration measured this time and the acetone concentration measured the previous time from the acetone concentrations measured in the past, and corresponding to the elapsed time from the time of the previous measurement to the time of the current measurement. However, the diet level may be determined based solely on the difference Δ. Moreover, the diet level may be determined not on the difference Δ between the acetone concentration measured this time and the acetone concentration measured the previous time, but by using a ratio between the acetone concentration measured this time and the acetone concentration measured the previous time.

In the present exemplary embodiment, at step S102 the poor physical condition level is determined based on the current acetone concentration measured at step S100, but the poor physical condition level may be determined by a method similar to the first diet level determination method. More specifically, a poor physical condition level determination standard similar to that of the diet level determination standard 40 illustrated in FIG. 5 may be prepared, and the poor physical condition level may then be determined based on a past acetone concentration, the current acetone concentration measured at step S100, and the poor physical condition level determination standard.

The diet level may be determined based only on the current acetone concentration. More specifically, a diet level determination standard similar to the poor physical condition level determination standard 30 illustrated in FIG. 4 may be prepared, and the diet level may be determined based on the current acetone concentration and the diet level determination standard.

In a second diet level determination method, when measurement results of acetone concentration before and after a mealtime within the same day are stored in the non-volatile memory 20D, the diet level is determined based on a comparison result between the acetone concentration measured before the meal and the acetone concentration after the meal.

Figure 6:
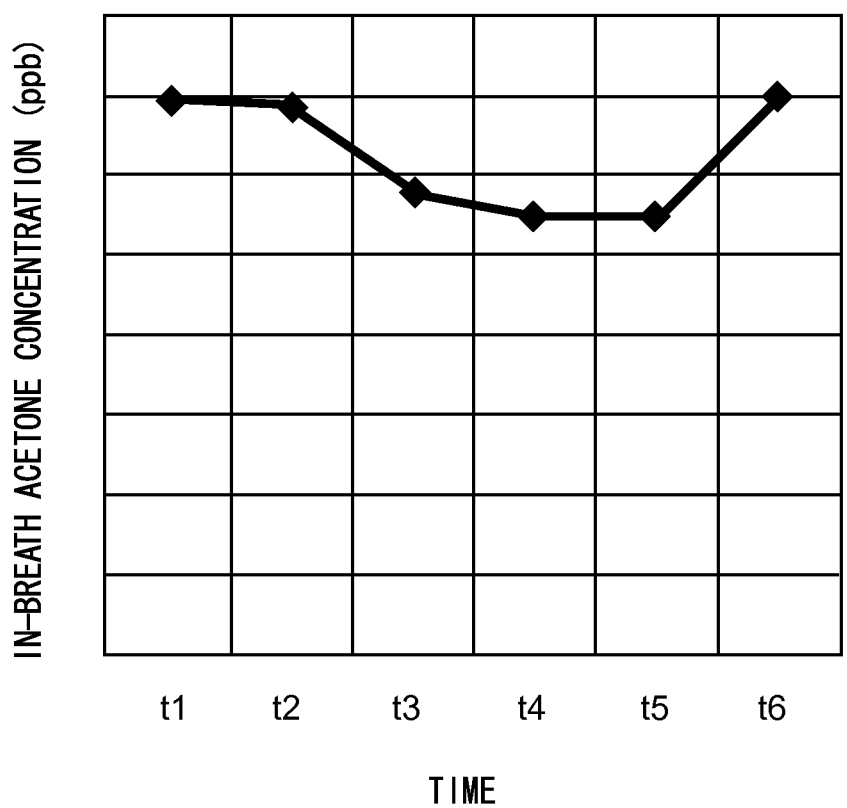
FIG. 6 is a graph illustrating an example of a variation curve of acetone concentration, showing a case in which acetone concentration falls after a meal.

FIG. 6 illustrates an example of a normal variation curve as an acetone concentration variation curve before and after a mealtime. As illustrated in FIG. 6, if a lunch mealtime is between times t2 and t3, then the acetone concentration gradually lowers after the meal if a good lunch is taken, and the acetone concentration then rises as the sugar energy in the body becomes insufficient.

Figure 7:
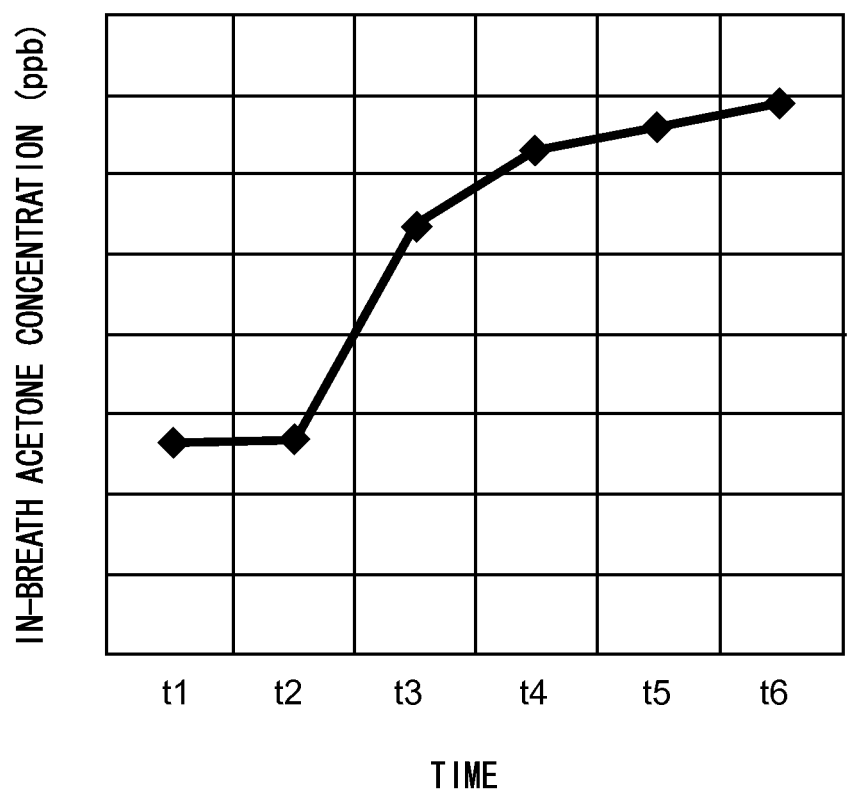
FIG. 7 is a graph illustrating an example of a variation curve of acetone concentration, showing a case in which a meal is not taken and a fall in acetone concentration cannot be observed.

However, when an excessive diet is embarked on and no lunch is taken, the acetone concentration does not fall even when lunchtime has passed, and instead continues to rise, as illustrated in FIG. 7.

For example, the difference (A−B) is obtained between the acetone concentration A before a meal and the acetone concentration B after a meal, and when the obtained difference is a positive value, namely if the acetone concentration B after a meal is less than the acetone concentration A before the meal, the diet level is determined to be normal. Determination is made that the diet level is abnormal when the difference (A−B) is a negative value, namely when the acetone concentration after a meal is the acetone concentration before the meal or greater.

The mealtimes may be predetermined such as, for example, breakfast at 07:00, lunch at 12:00, and supper at 19:00, or mealtimes may be input by a user and stored in the non-volatile memory 20D, and diet level determination performed by comparison of acetone concentrations before and after the mealtimes.

I the above case the diet level is determined as normal or abnormal based on the difference (A−B) between the acetone concentration A before a meal and the acetone concentration B after a meal; however the diet level may be determined as normal or abnormal based on a ratio (B/A) between the acetone concentration A before a meal and the acetone concentration B after a meal. In such cases the diet level is determined as normal in cases in which the ratio (B/A) is less than 1, namely when the acetone concentration after a meal is less than the acetone concentration before the meal, and the diet level is determined as abnormal in cases in which the ratio (B/A) is 1 or greater, namely when the acetone concentration after a meal is the acetone concentration before the meal or greater.

In a third diet level determination method, whether or not excessive dieting has occurred may be determined as the diet level when there are plural days of acetone concentration measurement results stored in the non-volatile memory 20D. When the acetone concentration is measured plural times during the same day, the average value of all the acetone concentrations measured within the same day may, for example, be taken as the acetone concentration for that day.

Figure 8:
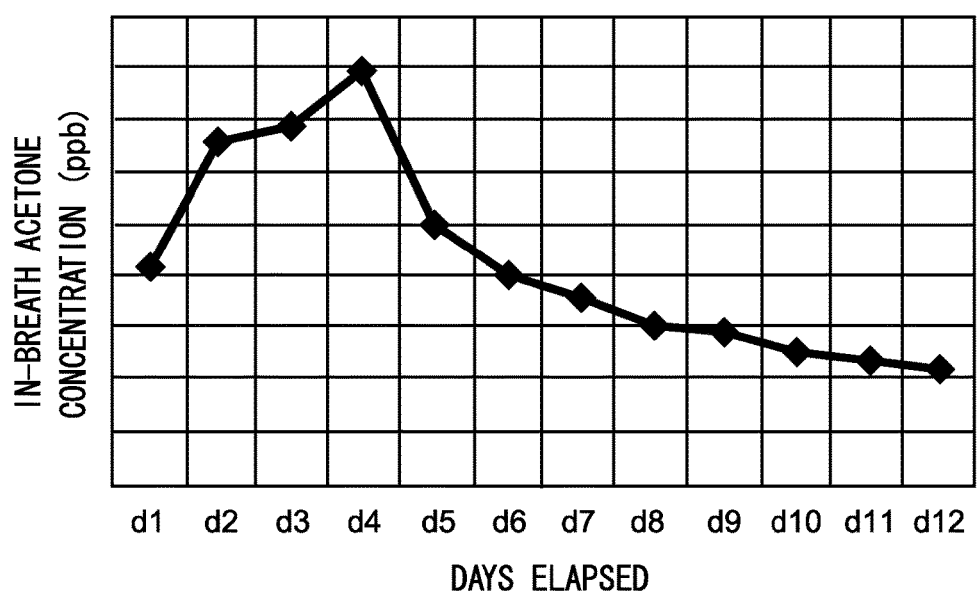
FIG. 8 is a graph illustrating an example of a variation curve of acetone concentration, showing a case in which acetone concentration falls due to a rebound.

FIG. 8 illustrates an example of a variation curve of acetone concentration when rebound has occurred due to excessive dieting. As illustrated in FIG. 8, a sharp rise in acetone concentration between day d1 and day d4 is thought to be an indication of excessive dieting. Determination as to whether or not excessive dieting is occurring may be made by determining whether or not there is a sharp rise in the acetone concentration measured during a predetermined period (for example over 4 days).

For determination as to whether or not there is a sharp rise, a sharp rise in acetone concentration is determined when $(A2-A1)/(D2-D1)$ is a predetermined first threshold value or greater, wherein A1 is the acetone concentration at a start day D1 of a period for determining whether or not there is a sharp rise, and A2 is the acetone concentration at the final day D2 thereof. Namely, a sharp rise is determined when the slope of a line connecting the acetone concentration of the start day of the period for determining whether or not there is a sharp rise and the acetone concentration at the final day thereof is the predetermined first threshold value or greater. Determination of a sharp rise may also be made when the difference $(A2-A1)$ between the acetone concentration A1 at the start day D1 of the period for determining whether or not there is a sharp rise, and the acetone concentration A2 at the final day D2 thereof is a predetermined second threshold value or greater, or when a ratio $(A2/A1)$ is a predetermined third threshold value or greater.

In a fourth diet level determination method, whether or not there a rebound has occurred is determined as the diet level based on measurement results of acetone concentration over plural days when the measurement results of acetone concentrations on plural days are stored in the non-volatile memory 20D.

The example in FIG. 8 illustrates a high acetone concentration state spanning from day d1 to day d4, namely a continuous state in which there is a lot of fat burning, and the high acetone concentration condition continuing during this period may be thought of as being due to dieting. After the acetone concentration then falls sharply from day d4 to day d5, the acetone concentration then gradually decreases, with a low acetone concentration state maintained. The maintained low acetone concentration state may be thought of as being due to excessive eating as a result of rebound and a low level of exercise. Namely, the acetone concentration variation curve when rebound occurs is a curve that falls rapidly after a high acetone concentration state has continued for a specific period of time, and then maintains a low acetone concentration state for another specific period of time.

Determination is made in such cases as to whether or not rebound has occurred by determining whether or not the acetone concentration variation curve (referred to below as the measurement curve) measured over a predetermined period (for example 12 days) is a curve (referred to below as a rebound curve) that falls rapidly after continuing at a high acetone concentration state for a specific period of time, and then maintains a low acetone concentration state for a specific period of time.

Whether or not there has been a sharp fall is determined by determining a sharp fall when $(A2-A1)/(D2-D1)$ is less than a predetermined fourth threshold value, wherein A1 is the acetone concentration at a start day D1 of a period for determining whether or not there is a sharp fall, and A2 is the acetone concentration at the final day D2 thereof. Namely, a sharp fall is determined when the slope of a line connecting the acetone concentration of the start day of the period for determining whether or not there is a sharp fall and the acetone concentration at the final day thereof is less than the predetermined fourth threshold value. Determination of a sharp fall may also be made when the difference $(A2-A1)$ between the acetone concentration A1 at the start day D1 of the period for determining whether or not there is a sharp fall, and the acetone concentration A2 at the final day D2 thereof, is less than a predetermined fifth threshold value, or determination of a sharp fall may also be made when a ratio $(A2/A1)$ is less than a predetermined sixth threshold value.

Moreover, for example, the similarity between the measurement curve and the rebound curve may also be calculated using a known method, and rebound determined to have occurred when the calculated similarity is a predetermined seventh threshold value or greater.

Figure 9:
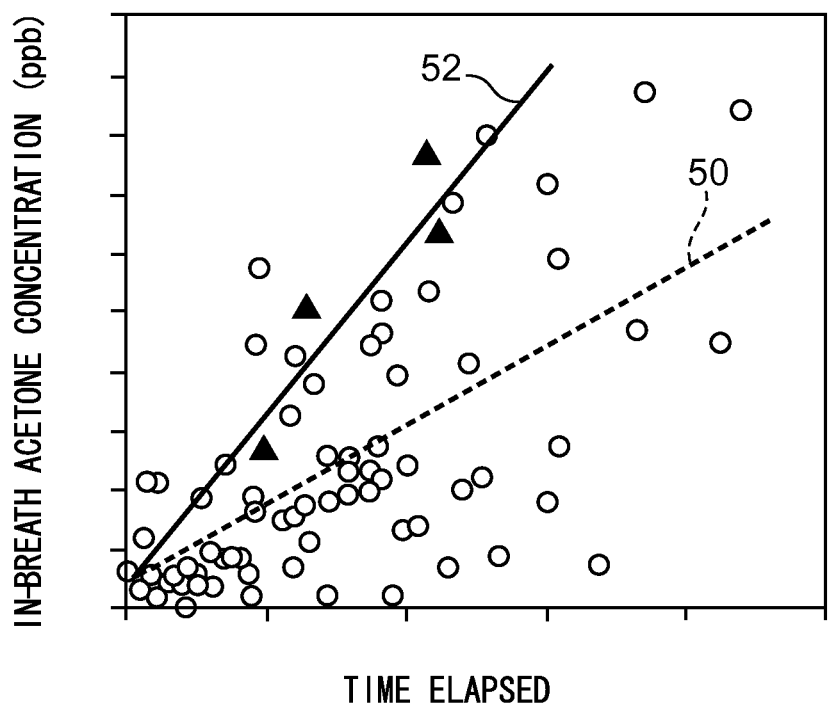
FIG. 9 is a graph explaining a slope of acetone concentration in people performing healthy dieting.

In a fifth diet level determination method, occurrence of excessive dieting is determined based on acetone concentration measurement results of many subjects performing healthy, namely normal, dieting. FIG. 9 illustrates a relationship between acetone concentration and elapsed time during a diet execution period of healthy dieting performed by many subjects.

In FIG. 9, points represented by white circles indicate acetone concentrations measured for many subjects who performed healthy dieting, giving a reference straight line 50 expressing a first order equation using, for example, a minimum sum of squares method. Points represented by black triangles are acetone concentrations of people who performed excessive dieting, giving a straight line 52 expressing a first order equation using, for example, a minimum sum of squares method.

As illustrated in FIG. 9, the slope of the straight line 52 is steeper than the slope of the reference straight line 50. Namely, due to the people who performed excessive dieting not eating suitable meals, their rate of acetone concentration rise is steeper than for people who performed healthy dieting eating suitable meals.

In this case, for example, a first order equation may be calculated from acetone concentrations measured plural times using a minimum sum of squares method, and excessive dieting determined when the slope of the straight line representing the calculated first order equation is steeper than the slope of the reference straight line 50.

Although the relationship between the acetone concentrations and elapsed time is represented by a first order equation above, the relationship may be represented using a quadratic equation, may be represented using a polynomial equation of third order or above, or using an equation that approximates better to actual values. The relationship between the acetone concentrations and elapsed time may also be represented by a data table instead of an equation. The average value or the standard deviation of acetone concentration measurement values from many subjects who performed healthy dieting may also be employed as a threshold value, and excessive dieting determined when the measured acetone concentration exceeds the respective threshold value.

At least one of diet level or poor physical condition level is determined based on at least one of the first to fifth evaluation methods described above, and the determination result stored in the non-volatile memory 20D together with the current time.

Although in the present exemplary embodiment explanation has been given of cases employing the first to fifth evaluation methods, the evaluation method is not limited thereto.

At step S110, the determination result at step S108, and advice information corresponding to the determination result, is displayed on the display section 14. For example, a data table expressing correspondence relationships between determination results and advice information may be stored in the non-volatile memory 20D, and the advice information extracted from the data table displayed on the display section 14. A message urging excessive dieting to be abandoned, for example "You are dieting too hard! Make sure you eat suitable meals!" may be displayed when excessive dieting has been determined. This thereby enables a user to perform a suitable diet, without excessive dieting. Configuration may be made such that the determination result is notified by at least one of light, vibration, or an alert sound.

The occurrence of excessive dieting is thereby determined simply by measuring the acetone concentration, and advice information displayed, thereby facilitating notification to a user of whether or not excessive dieting is occurring, and enabling warning of poor physical condition to be given.

Figure 10:
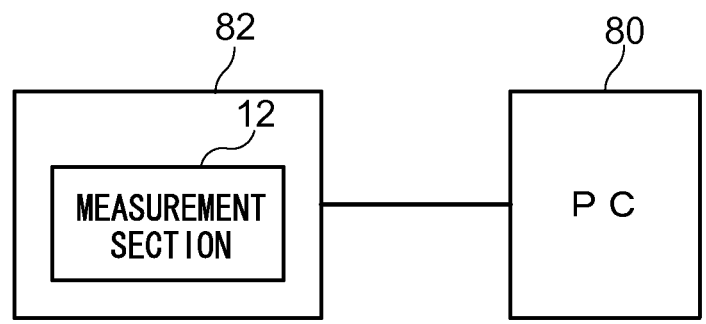
FIG. 10 is a block diagram illustrating a connection between a measurement instrument and a personal computer.

Although explanation has been given in the present exemplary embodiment regarding a case in which the poor physical condition determination device 10 is a dedicated portable device, configuration may be made in which a measurement instrument 82 including a measurement section 12 is connected by wire, or wirelessly, to a personal computer 80, as illustrated in FIG. 10. In such cases the personal computer 80 functions as a poor physical condition determination device by acquiring an acetone concentration measured by the measurement instrument 82, and executing the processing illustrated in FIG. 3.

The device connected to the measurement instrument 82 is not limited to a personal computer, and may be a portable terminal such as a mobile phone, a smart phone, or a tablet terminal. The measurement section 12 may also be built into such a portable terminal. Configuration may be made such that a portable terminal or the measurement instrument 82 is connected to a server over a network. In such cases the server functions as the poor physical condition determination device. Namely, the portable terminal or the measurement instrument 82 transmits the measured acetone concentration to a server, the server then executes the processing illustrated in FIG. 3 based on the acetone concentration received from the portable terminal or the measurement instrument 82, and transmits the result to the portable terminal or the measurement instrument 82. The measurement instrument 82 may thereby be provided with minimum functionality of measuring and transmitting the acetone concentration to the server, and functionality to receive the result from the server and display, enabling a cost effective configuration to be achieved.

Explanation has been given in the present exemplary embodiment regarding a case in which the measurement section 12 is configured including an acetone detection sensor that detects in-breath acetone, but there is no limitation thereto, and configuration may be made in which a ketone detection sensor is provided that detects excreted ketone, such as in the skin, urine, saliva, or sweat of a user.

What is claimed is:

1. A poor physical condition determination device comprising:
   ketone concentration acquisition section that acquires a ketone concentration measurement measuring ketone excreted from a user;
   a determination section that is programmed to determine an occurrence of excessive dieting based on at least one ketone concentration measurement measured in the past and including the ketone concentration measurement; and
   an output section that outputs a determination result by the determination section, wherein:
   the determination section is programmed to determine the occurrence of excessive dieting based on a difference or ratio between the ketone concentration measurement measured a previous time and the ketone concentration measurement measured this time, and elapsed time from the previous measurement to the current measurement.

2. A poor physical condition determination device comprising:
   ketone concentration acquisition section that acquires a ketone concentration measurement measuring ketone excreted from a user;
   a determination section that is programmed to determine an occurrence of excessive dieting based on at least one ketone concentration measurement measured in the past and including the ketone concentration measurement; and
   an output section that outputs a determination result by the determination section, wherein:
   the determination section is programmed to determine the occurrence of excessive dieting based on a comparison result between the ketone concentration measurement measured before a meal and the ketone concentration measurement measured after a meal, and the determination section is programmed to determine the occurrence of excessive dieting when the ketone concentration measurement measured after a meal is higher than the ketone concentration measurement measured before a meal.

3. A poor physical condition determination device comprising:

ketone concentration acquisition section that acquires a ketone concentration measurement measuring ketone excreted from a user;

a determination section that is programmed to determine an occurrence of excessive dieting based on at least one ketone concentration measurement measured in the past and including the ketone concentration measurement; and an output section that outputs a determination result by the determination section, wherein:

the determination section is programmed to determine whether or not a rebound has occurred based on a determination of whether a curve representing ketone concentration measurements over a period of time begins high, falls rapidly, and then remains low.

4. The poor physical condition determination device of claim 1, further comprising a measurement section that measures ketone excreted from the user.

5. The poor physical condition determination device of claim 1, wherein the ketone excreted from the user are acetone contained in breath exhaled from the user.

6. A poor physical condition determination method using the poor physical condition determination device of claim 1, comprising:

acquiring a ketone concentration measurement measuring ketone excreted from a user;

determining the occurrence of excessive dieting based on the acquired ketone concentration measurement; and outputting a determination result.

7. A non-transitory recording medium stored with a poor physical condition determination program that causes processing to be executed on a computer in the poor physical condition determination device of claim 1, the processing comprising:

acquiring a ketone concentration measurement measuring ketone excreted from a user;

determining the occurrence of excessive dieting based on the acquired ketone concentration measurement; and outputting a determination result.

8. The poor physical condition determination device of claim 1, wherein:

the determination section is programmed to determine a diet level based on a difference between the ketone concentration measurement measured a previous time and the ketone concentration measurement measured this time, and elapsed time from the previous measurement to the current measurement, the determination section is programmed to determine that the diet level is a first level when the ketone concentration measurement measured this time is less than 1,000 ppm greater than the ketone concentration measurement measured in the previous time and the elapsed time between this time and the previous time is one day or less, and the determination section is programmed to determine that the diet level is a second level when the ketone concentration measurement measured this time is less than 1,000 ppm greater than the ketone concentration measurement measured in the previous time and the elapsed time between this time and the previous time is two to four days.

9. The poor physical condition determination device of claim 2, further comprising a measurement section that measures ketone excreted from the user.

10. The poor physical condition determination device of claim 2, wherein the ketone excreted from the user are acetone contained in breath exhaled from the user.

11. The poor physical condition determination device of claim 3, further comprising a measurement section that measures ketone excreted from the user.

12. The poor physical condition determination device of claim 3, wherein the ketone excreted from the user are acetone contained in breath exhaled from the user.

* * * * *